(12) United States Patent
Randhava et al.

(10) Patent No.: US 8,546,454 B2
(45) Date of Patent: Oct. 1, 2013

(54) PROCESS AND METHOD FOR THE PRODUCTON OF DIMETHYLETHER (DME)

(75) Inventors: Sarabjit S. Randhava, Evanston, IL (US); Richard L. Kao, Northbrook, IL (US); Todd L. Harvey, Schaumburg, IL (US)

(73) Assignee: Unitel Technologies, Inc., Mount Prospect, IL (US)

( * ) Notice: Subject to any disclaimer, the term of this patent is extended or adjusted under 35 U.S.C. 154(b) by 313 days.

(21) Appl. No.: 13/190,678

(22) Filed: Jul. 26, 2011

(65) Prior Publication Data

US 2013/0030063 A1  Jan. 31, 2013

(51) Int. Cl.
*C07C 27/00* (2006.01)
(52) U.S. Cl.
USPC ............ 518/700; 518/702; 518/703; 518/704

(58) Field of Classification Search
USPC .......................................... 518/700, 703, 704
See application file for complete search history.

(56) References Cited

U.S. PATENT DOCUMENTS

2010/0040510 A1* 2/2010 Randhava et al. ............ 422/140

* cited by examiner

*Primary Examiner* — Jafar Parsa

(57) ABSTRACT

Disclosed herein is a process for the production of fuel grade DME from carbonaceous fuels, including a pressurized multi-stage progressively expanding fluidized bed gasifier and an oxyblown autothermal reformer to produce a synthesis gas (syngas) with desirable hydrogen to carbon monoxide molar ratio, which then undergoes gas-phase DME one-step direct synthesis in a fluid pluralized bed reactor over an attrition resistant bifunctional catalyst. The crude DME thus obtained is purified in a two column distillation unit to produce a fuel grade DME having a purity greater than 99.98 mole %.

13 Claims, 7 Drawing Sheets

Loading Characteristics for Chemical & Physical Solvents

PROCESS AND METHOD FOR THE PRODUCTON OF DIMETHYLETHER (DME)

REFERENCES CITED

U.S. Pat. No. 4,417,000 Nov. 22, 1983 Lynn H. Slaugh et al.
U.S. Pat. No. 5,037,511 Aug. 6, 1991 Horst Dornhagen et al.
U.S. Pat. No. 6,485,856 B1 Oct. 1, 2002 Xiang-Dong Peng el al.
U.S. Pat. No. 6,608.,114 B1 Aug. 19, 2003 Edward C. Heydorn et al.
U.S. Patent Application Publication No. 2004/0176481 A1 Sep. 9, 2004 Alain Guillard et al.
U.S. Patent Application Publication No. 2006/0052647 A1 Mar. 9, 2006 Tsutomu Shikada el al.
U.S. Patent Application Publication No. 2008/0027150 A1 Jan. 31, 2008 Andre Peler Stcynbcrg
Voss, Bodil, DK; Joensen, Finn, DK; Bogild, Hansen, John, DK; *Preparation D-Ether Dimethytique de Qualite Carburant*, Brevet-Patent 2,211,722, Mar. 2, 1995
Peng, X.D.; Toseland, B.A.; Wang A.W.; Parris, G.E., *Progress in Development of LPDME Process: Kinetics and Catalysts*, 1997 Coal Liquefaction & Solid Fuels Contractors Review Conference, Sepl. 3-4, 1997
Lu, W.Z., Teng. L.H., Xiao, W.D., Simulation and experiment study of dimethyl ether synthesis from syngas in a fluidized-bed reactor. Chemical Engineering Science 59,5455-5464, 2004
Teng, L.H., *Attrition Resistant Catalyst for Dimethyl Ether Synthesis in Fluidized-Bed Reactor*, Journal of Zhejian University Science A, 9(9), 1288-1295,2008

FIELD OF THE INVENTION

The present invention relates, generally, to a process for the production of dimethylether (DME) from syngas in a fluid pluralized bed reactor over an attrition resistant bifunctional catalyst. This syngas is produced from carbonaceous fuels through a pressurized multi-stage progressively expanding fluid bed gasifier coupled with an oxyblown autothermal reformer.

BACKGROUND OF THE INVENTION

DME is non-toxic and is currently used as aerosol propellants and refrigerant as a substitute of chlorofluorocarbons. The property of DME is very attractive as a substitute of LPG and diesel oil and as a clean fuel without SOx and smoke.

DME's boiling point at ambient pressure (−24.6° C.) is below minus and close to LPG as $C_3H_8$ (−42.1° C.) which is easily liquefied and stored. LPG existing infrastructure such as tank and refrigerated tanker could be used with minor modification. DME cetane number (55-60) is very similar to diesel oil (38-53). DME could be used in diesel engines with minor modification.

DME is currently produced indirectly by dehydration of methanol in small scale plants in total with an order of 250,000 MT/Y in the world. On the contrary, DME is multi-source energy and could be mass-produced directly in one step from syngas converted from various feedstocks such as natural gas, fuel oil, coal, biomass, etc. Recently there are announcements of many projects being planned to start commercial operation using the DME direct synthesis route.

In this invention, a process of economically and efficiently producing DME in direct route is disclosed.

SUMMARY OF THE INVENTION

It is the object of the present invention to provide a process of economically and efficiently producing DME, which comprises converting carbonaceous fuel into syngas, which then undergoes gas-phase DME direct synthesis.

In order to accomplish the above object, the present invention provides a process for the production of DME comprising the following steps of:

Simultaneously subjecting a feedstock mixture including carbonaceous fuel, steam, oxidant to a pressurized multi-stage progressively expanding fluidized bed gasifier to eliminate or reduce the formation of methane gas and tars;

Using an oxyblown autothermal reformer to reform any residual tars and benzene, toluene and xylenes that are still present in the hot gases into additional syngas. The autothermal reformer may also convert most of the methane present in the gasifier effluent stream into additional syngas;

Recovering the heat from the reformer effluent in the syngas heat recovery boiler;

Directing the effluent from the syngas heat recovery boiler into a water cooled heat exchanger where the bulk of the water vapor in the syngas is condensed and knocked-out;

Compressing the cooled syngas from 130 psig (10 bar) to 710 psig (50 bar) which is the desirable pressure for the acid gas removal system;

Directing the compressed syngas into the acid gas absorber where the acid gas content in the syngas is removed to a desirable level;

Subjecting the treated syngas to the DME synthesis in the presence of a catalyst to obtain a reaction product gas mixture including DME, methanol, carbon dioxide, water vapor, unconverted hydrogen and carbon monoxide;

Condensing the reaction product gas mixture to separate part of the DME product and most of the water produced;

The balance of the DME product and most of the carbon dioxide produced is recovered by a methanol or methanol/DME absorber operating at absorber outlet temperatures ranging from −6° F. (−21° C.) to 23° F. (−5° C.);

Purifying the above two crude DME streams to obtain the fuel grade DME product.

DETAILED DESCRIPTION OF THE INVENTION

Syngas Production Options

Figure 1:
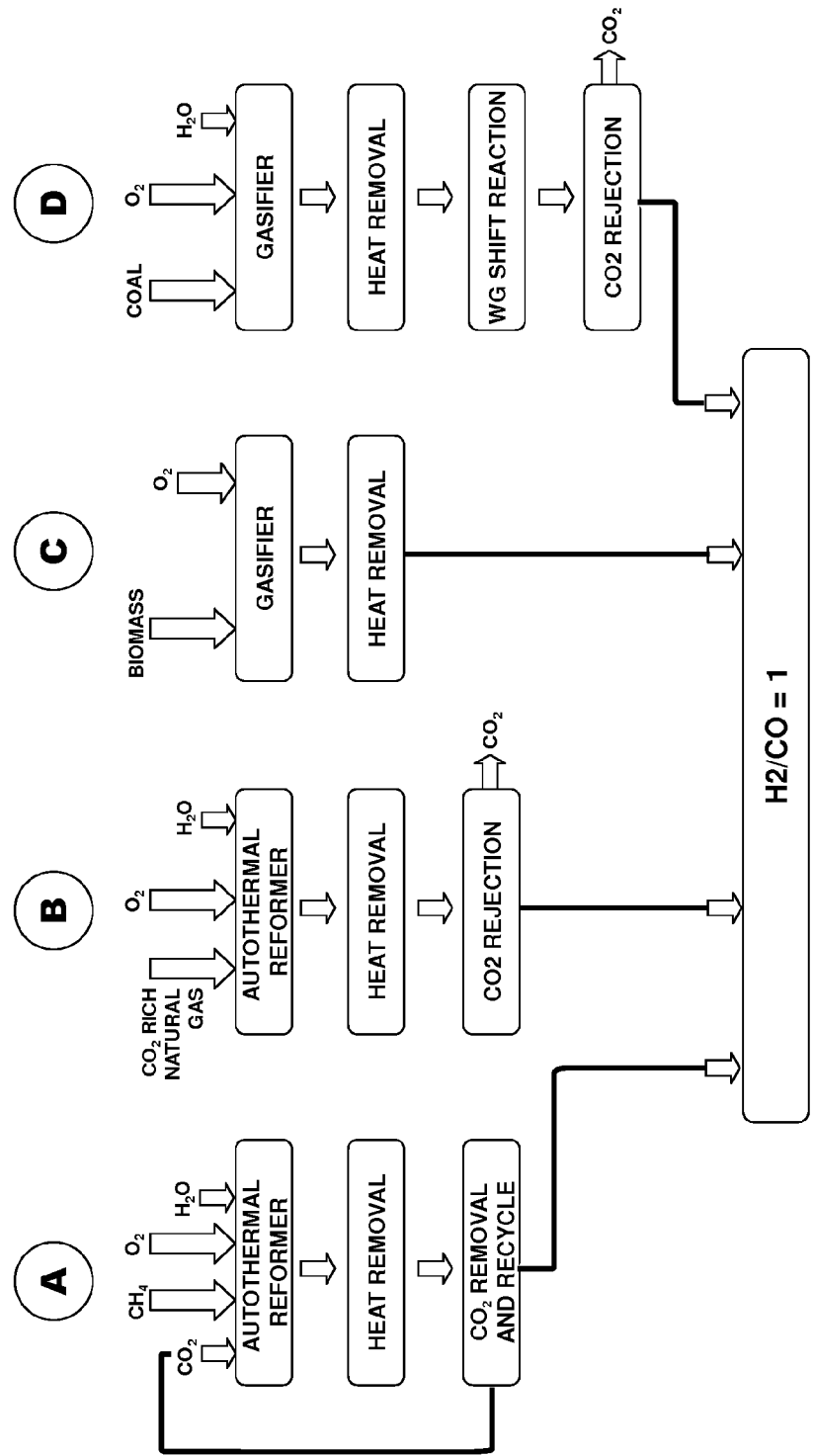
FIG. 1 illustrates syngas production options.

Irrespective of the feedstock category, the objective of the synthesis gas production step is to make the $H_2$/CO molar ratio as close to 1.0 as possible. Four options for achieving this goal are schematically represented in FIG. 1.

Every route for making syngas entails the use of oxygen. Depending upon the category and exact properties of the feedstock, a good thumb rule is that you will need approximately 1.0 to 1.1 ton of oxygen per ton of DME produced.

Autothermal Reforming Overview

---
Category A: Natural gas available in small (stranded) or large (world-scale) quantities
Category B: CO2 rich stranded natural gas or biogas
Uses Autothermal Reforming Technology
---

It is now widely accepted that, as a result of technology improvements over the years, the modern autothermal reformer is a more cost-effective method than steam reforming for making syngas. Conventional autothermal reforming uses a two-step reactor in which the inputs are first reacted in a homogeneous partial combustion section, followed by an independent steam reforming section. In spite of its advantages over pure steam reforming, this approach is quite unforgiving in terms of upsets and changes in operating conditions. A high level of attention is required to prevent coking and shutdown for other reasons.

Feature speakers at a recent DeWitt Global Methanol & Clean Fuels Conference confirmed the belief that in the future autothermal reforming will be the preferred alternative to steam reforming. As a matter of fact, the consensus is that no more steam reformers will be built for world scale methanol and DME plants.

In this invention, we use an integrated autothermal reformer in which the partial oxidation and steam reforming are conducted simultaneously. A proprietary heterogeneous catalyst is used to enable these reactions. The reformer does not require a burner, is capable of highly stable operation, and can be easily fine-tuned to produce a gas mixture with a hydrogen to CO molar ratio of 1.0. $CO_2$ is recovered immediately downstream of the reformer. Depending upon the feedstock being used, this $CO_2$ is either recycled back into the reformer, or is vented into the atmosphere.

Some ideal design targets for autothermal reforming are:
S/G ratio of 0.6 to 0.8
Outlet temperatures of 955° C. to 1050° C. (1751° F. to 1922° F.)
Design pressures of 15 to 30 bars (203 psig to 420 psig)

There are two common sources of natural gas that are optimal for this application: natural gas or $CO_2$ containing methane. These sources are world scale gas fields, stranded gas and flared gas.

In this process, $CO_2$ laden moist natural gas stream is created by blending two streams: the first stream is created by recovering $CO_2$ from the syngas stream using moist natural gas and the second stream is created by recovering $CO_2$ after the DME synthesis reaction also using moist natural gas. This consolidated stream is directed into a hydrodesulfurizer where the sulfur containing compounds are converted into hydrogen sulfide which is adsorbed in a bed of zinc oxide. This clean methane and $CO_2$ stream is passed into a pre-reformer along with a separate stream of steam, which has been generated in a heat recovery unit. A certain controlled amount of conversion of methane into hydrogen/CO is conducted at temperatures of around 450° C. (842° F.). The intent of the pre-reformer is to decrease the load on the subsequent reforming reactor.

This consolidated clean gas flow is then directed to the entry nozzle of the autothermal reformer. Oxygen at pressure is warmed up in the convection section of a gas fired heater and also directed into the autothermal reformer entry nozzle. The temperatures are maintained such that a partial oxidation reaction can readily occur. The autothermal reformer comprises of a monolithic catalyst incorporated within an insulated pressure vessel. The monolithic catalyst is based upon an overlap reaction zone concept where a double layer of catalyst has been incorporated upon a corderite substrate. The lower section of the double layer is formulated to enable catalytic steam reforming while the upper section is formulated to provide catalytic partial oxidation. Consequently, it is easy to visualize the operating scenario where the exothermic catalytic partial oxidation reaction is on-going and generating heat that is utilized by the endothermic steam reforming going on right below. Appropriate ratios of partial oxidation to steam reforming catalyst can be incorporated to minimize the net axial rise in temperature. This is significant because there is not much latitude available in the maximum temperature that the catalyst can sustain over a long period of time.

A typical exit temperature of 955° C. (1751° F.) at a pressure of 150 psig (11 bar) to 250 psig (18 bar) is appropriate to minimize methane in the affluent down to controllable concentrations. This hot syngas is cooled down in waste heat recovery units (superheated steam is recovered at the same time) and a significant quantity of water is condensed out and rejected out of the system. The dewatered syngas stream is then compressed to a pressure of around 710 psig (50 bar).

Gasification Overview

---
Category C: Biomass rich in carbon also containing chemically bound oxygen
Category D: Carbonaceous materials very low in chemically bound oxygen
Uses Gasification Technology
---

Gasification is a process by which either a solid or liquid carbonaceous material, containing mostly chemically bound carbon, hydrogen, oxygen, and a variety of inorganic and organic constituents, is reacted with air, oxygen, and/or steam. The reactions provide sufficient exothermic energy to produce a primary gaseous product containing mostly CO, $H_2$, $CO_2$, $H_2O$ vapor, and light hydrocarbons laced with volatile and condensable organic and inorganic compounds. Most of the inorganic constituents in the feedstock are chemically altered and either discharged as bottom ash or entrained with the raw product gas as fly-ash. The gas is cooled, filtered, and scrubbed with water or a process-derived liquid to remove condensables and any carry-over particles. Brown coal, when gasified with steam and/or oxygen, will produce raw syngas rich in CO and $H_2$. Generally, this raw syngas undergoes particulate gas clean-up using cyclones and other positive devices. Subsequent to the particular clean-up, the issue of tar reduction and/or mitigation must be conducted using appropriate optimal protocols. This cleaned gas is referred to as syngas and utilized appropriately.

Based upon evolutionary development, modern gasification technologies generally fall into three categories:
Fluidized bed
Moving bed
Entrained flow These three basic gasifier designs—originally developed in the 1950's—were all re-engineered in the 1970's and 1980's to operate under higher pressures. It should be noted that higher pressures increase the productive capacity of the gasifier and enable a wider range of syngas applications.

Fluidized Bed

The fuel, introduced into an upward flow of steam/oxygen, remains suspended in the gasifying agents while the gasification process takes place. Since the operating temperature of the reactor, 800° C. to 1,050° C. (1,472° F. to 1,922° F.), is generally less than the temperature at which the ashes from the fuel melt, these can be removed either in dry form or as agglomerate. In case a molten ash formed, it can be removed in a similar way to the entrained flow gasifier.

Moving Bed

This carbonaceous fuel is dry-fed through the top of the reactor. As the fuel slowly descends, it reacts with the gasifying agents (steam and oxygen) flowing in a counter-currently through the bed. This fuel goes through the various stages of gasification unit it is ultimately consumed, leaving only syngas and a dry ash. The syngas has a low temperature, 400° C. to 500° C. (752° F. to 932° F.), and contains significant quantities of tars and oils. This technology is generating decreasing market interest.

Entrained Flow

The fuel and gasifying agents flow in the same direction (and at rates in excess of other gasifier types). The feedstock—which may be dry-fed (mixed with nitrogen) or wet-fed (mixed with water)—goes through various stages of gasification as it moves with the steam/oxygen flow. The syngas exits through the top of the reactor and the ashes flow down the sides as a molten slug, which is removed from the bottom. Operating temperatures are very high, 1,200° C. to 1,600° C. (2,192° F. to 2,912° F.).

This invention provides systems and methods for converting fuel into syngas using a pressurized multi-stage progressively expanding fluidized bed gasifier to eliminate or reduce the formation of methane and tars. The fluidized bed may contain a fluidizing medium that may range from sand to olivine particles. Olivine has the additional benefit of being able to convert a significant amount of tars into syngas.

This invention also discloses the use of an oxyblown autothermal reformer downstream of the gasifier. In this oxyblown autothermal reformer, any residual tars and benzene, toluene and xylenes that are still present in the hot gases may be reformed into additional syngas. The autothermal reformer may also convert most of the methane present in the gasifier effluent stream into additional syngas. This reformer may enable the maintenance of high syngas temperatures, 780° C. to 850° C. (1,436° F. to 1,562° F.) for efficient heat recovery.

The gasifier may include a plurality of stages, where a subsequent stage may be in fluid communication with a previous stage. In some embodiments, the subsequent stage may have a greater cross-sectional area than the previous stage. Any number of stages may be provided. In some instances, two, three, four, five or more stages may be provided. For example, one or more reaction stage, fluidization bed stage, and disengagement stage may be provided. A pressurized gasifier may be configured such that the chemical kinetics within the reaction zone, and the geometry of its multiple stages and inter-stage transitions may facilitate to reduce the formation of methane and tars.

Various aspects of the invention described herein may be applied to any of the particular applications set forth below or for other types of gasification systems. The invention may be applied as a standalone system or method, or as part of an application, such as a gas production plant. It shall be understood that different aspects of the invention can be appreciated individually, collectively, or in combination with each other.

Water Knock-Out & Syngas Compression

The gas leaving the syngas heat recovery boiler may be hot, e.g., around 204° C. (400° F.) and may contain a significant quantity of water vapor. It is directed into a water cooled heat exchanger where the bulk of the water vapor may be condensed, collected and purified for reuse as boiler feed water. The cooled gases may flow to a compressor at a pressure of around 10 bar (130 psig). They may be compressed to an increased exit pressure, e.g., around 50 bar (710 psig) which may be an optimum or desirable pressure for the acid gas removal system.

Acid Gas Removal

Figure 2:
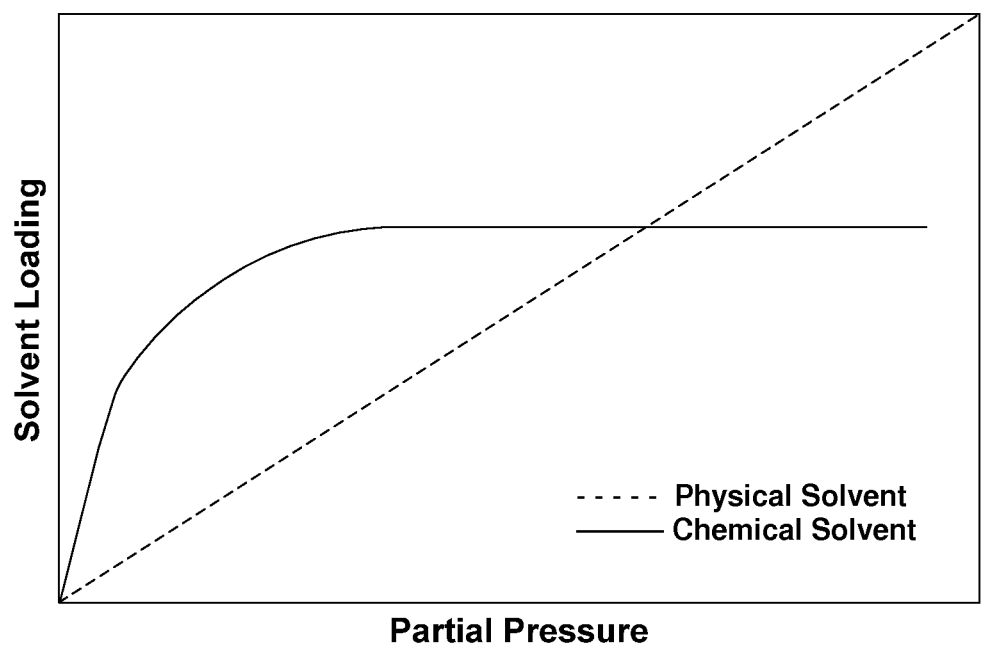
FIG. 2 is the loading characteristics for chemical & physical solvents.

A number of technologies are available for acid gas removal including chemical solvents, physical solvents, mixtures of physical/chemical solvents and membranes. The two most applicable technologies for acid gas removal in Gasification facilities are chemical solvents and physical solvents. Chemical solvents, such as methyldiethanolamine (MDEA) and diethanolamine (DEA), have high absorption capacity at relatively low acid gas partial pressures. However, the absorption capacity plateaus at higher partial pressures. The solubility of acid gases in physical solvents increases linearly with acid gas partial pressure (FIG. 2). Therefore, chemical solvent technologies are favorable at low acid gas partial pressures and physical solvents are favored at high acid gas partial pressures. Furthermore, the physical absorption allows for the solvent to be regenerated by pressure reduction, which reduces the energy requirement. The chemical solvents react to form a chemical bond between the acid gas and the solvent with the tendency to form heat-stable salts that plague the chemical solvent system. For a chemical absorption system, huge energy consumption is required to regenerate the chemical solvent along with a high fresh solvent make-up rate to cover degradation and losses.

The physical solvent $CH_3-O-(CH_2CH_2O)_5-CH_3$ or $C_{12}H_{26}O_6$ is selected to be the solvent for this application. As compared to a chemical solvent, a well engineered physical solvent system could drop the cost of this unit operation by a significant margin both in terms of capital cost and in terms of variable cost due to the fact that it is a simpler unit and uses much less energy. The typical feed gas to and treated gas from the absorber is summarized in Table 1.

TABLE 1

TYPICAL FEED GAS TO & TREATED GAS FROM THE ACID GAS ABSORBER

| | MOLE % | |
|---|---|---|
| COMP. | FEED GAS | TREATED GAS |
| $CH_4$ | 2.36 | 2.27 |
| $CO_2$ | 17.43 | 2.70 |
| $N_2$ | 0.41 | 0.48 |
| $H_2O$ | 0.20 | 0.02 |
| CO | 40.69 | 47.47 |
| $H_2$ | 38.90 | 47.06 |
| $H_2S$ | 107 PPM | 0 |
| COS | 5 PPM | 0 |
| $NH_3$ | 41 PPM | 0 |
| TOTAL | 100.00 | 100.00 |
| $H_2$/CO Molar Ratio | 0.9560 | 0.9916 |
| Temperature, ° F. | 108.0 | 108.0 |
| Pressure, psig | 710.5 | 710.5 |

The typical treated gas (Table 1) from the acid gas absorber still contains 2.70 mole % of $CO_2$ that is required to retain the activity of the methanol synthesis catalyst. There is a sulfur guard located between the outlet of the acid gas removal system and the inlet of the DME synthesis loop to remove any trace amount of sulfur compounds that are still present in the treated gas.

The rich solvent exiting the Acid Gas Absorber is flash regenerated down to 1 bar (−0.2 psig) in a single flash drum.

The flash gas is sent to a furnace as fuel. The lean solvent is then pumped back to the Acid Gas Absorber for reuse. Table 2 presents the typical composition of the rich and lean solvents.

TABLE 2

TYPICAL RICH & LEAN SOLVENT COMPOSITION

| COMP. | MOLE % | |
|---|---|---|
| | RICH SOLVENT | LEAN SOLVENT |
| $CH_4$ | 0.36 | 92 PPM |
| $CO_2$ | 10.43 | 1.13 |
| $N_2$ | 0.02 | 2 PPM |
| $H_2O$ | 0.50 | 0.45 |
| CO | 2.21 | 189 PPM |
| $H_2$ | 1.29 | 65 PPM |
| $H_2S$ | 76 PPM | 18 PPM |
| COS | 4 PPM | 1 PPM |
| $NH_3$ | 31 PPM | 9 PPM |
| $C_{12}H_{26}O_6$ | 85.18 | 98.38 |
| TOTAL | 100.00 | 100.00 |
| Temperature, °F. | 112.6 | 108.0 |
| Pressure, psig | 710.5 | 710.5 |

Figure 3:
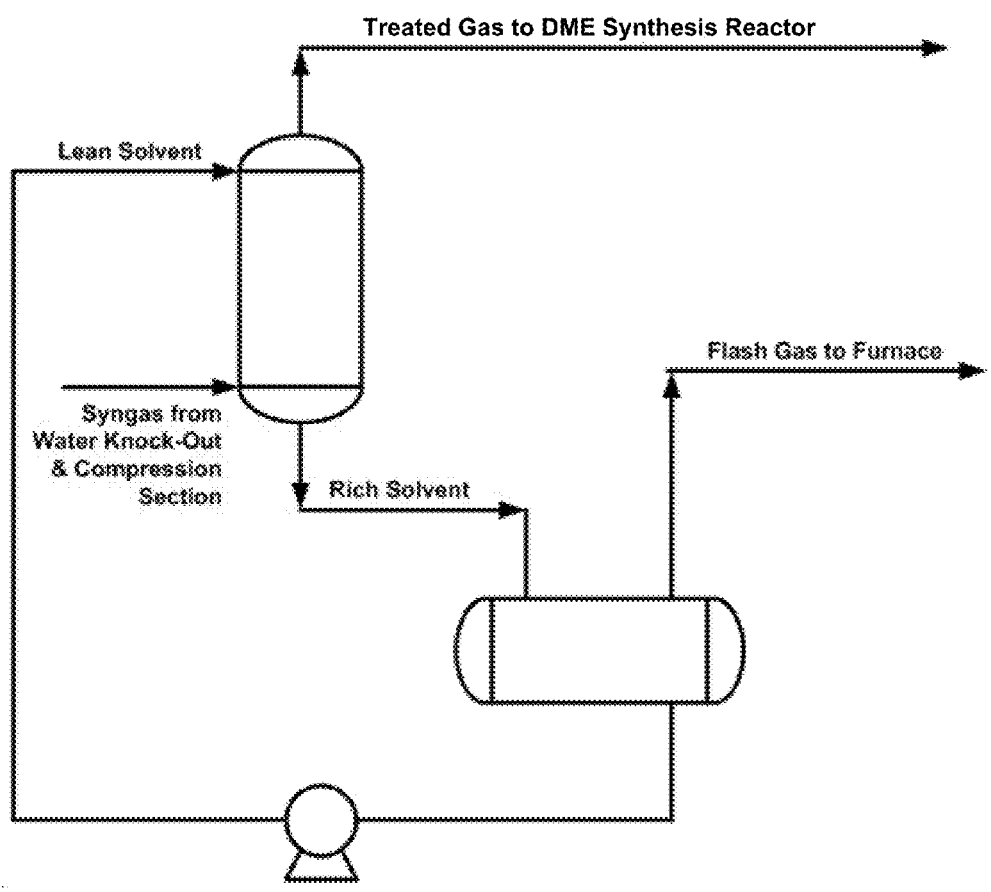
FIG. 3 is a simplified PFD for the acid gas removal process.

As shown in FIG. 3, syngas from the water knock-out & compression section enters the Acid Gas Absorber where it is contacted with lean physical solvent. $CO_2$ is removed from the syngas to below 2.70 mole %. The recycle pump is circulating the physical solvent at a suction pressure slightly higher than 1 bar (−0.2 psig) and a discharge pressure of about 50 bar (710 psig).

DME Synthesis

General Chemistry of DME Synthesis

The process of making dimethylether (DME) from a hydrogen and carbon monoxide syngas mixture is a strongly exothermic and equilibrium dictative reaction. Under LeChatelier principles, this process requires relatively high operating pressures and low temperatures to attain reasonable rates of reaction.

| | ΔH | Exothermic Heat |
|---|---|---|
| Methanol Synthesis from CO<br>$2CO + 4H_2 \Leftrightarrow 2CH_3OH$ (1) | −197.48 kJ/mole* | 74% |
| Methanol Dehydration to DME<br>$2CH_3OH \Leftrightarrow CH_3OCH_3 + H_2O$ (2) | −21.26 kJ/mole | 10% |
| Water Gas Shift<br>$CO + H_2O \Leftrightarrow CO_2 + H_2$ (3) | −39.57 kJ/mole | 16% |
| Overall DME Synthesis Reaction<br>Direct DME from Syngas<br>Producing $CO_2$<br>$3CO + 3H_2 \Leftrightarrow CH_3OCH_3 + CO_2$ | −258.31 kJ/mole | 100% |

*1 KJ/mole = 430.21 Btu/lb mole

All the three reactions are reversible and release a significant amount of heat for all these forward reactions. Consequently, a critical factor for DME reactor design is the management of the heat released by the reactions. The heat released by DME production can generate 2.4 tons of steam per ton of DME, equivalent to an adiabatic temperature rise of about 1,000° C. (1,832° F.) at a complete conversion of syngas with a 1:1 molar ratio of $H_2$:CO in the feed gas. However, the catalyst for Reactions (1) and (3) is subject to severe deactivation when overheated to above 280° C. (536° F.). To avoid thermodynamic limitations and excessive catalyst deactivation, conventional gas-phase reactors must be operated at a low per-pass conversion to maintain reactor temperature below 280° C. (536° F.), implementing a high syngas recycle rate, and resulting in large capital investments and operating costs.

Under such reaction conditions, the attainable conversion is strongly limited by the thermodynamic equilibrium. Finding a satisfactory compromise as to the reaction conditions between reaction rate and conversion percentage is therefore difficult. Effective control of the reaction temperature across the catalyst bed proved to be a technically problematic consideration.

In industrially applied processes, in which the catalyst is present in the form of a fixed bed of particles, high gas velocities are applied to promote effective removal of reaction heat and to allow good control of the reaction temperature. Due to these high velocities and the thermodynamic limitations, low CO conversions per pass are obtained. To achieve acceptable yields of DME from syngas it is customary to recompress unconverted syngas and recycle it to the reactor inlet. This requires recycle compressors of large capacities, which are costly and have high power consumptions.

It is because of these constraints that using a fluid pluralized bed becomes an optimal solution.

Fluidization

The description of fluidization, its characteristics and attributes are based upon the seminal work of D. Kunii and O. Levenspiel, Fluidization Engineering, 1977.

Figure 4:
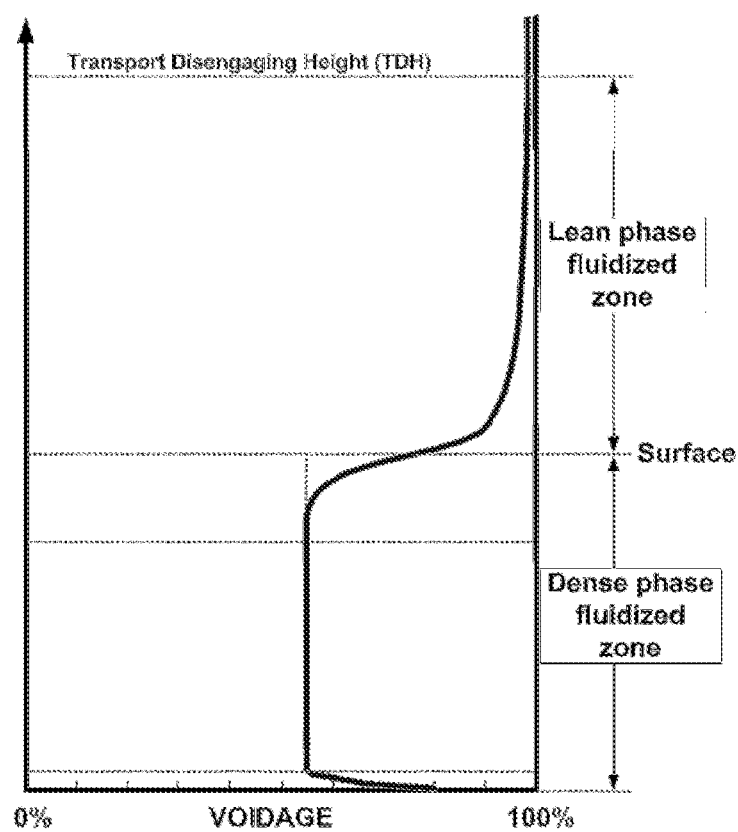
FIG. 4 is the voidage variation along the height of a fluid pluralized bed.

Voidage variation along the height of a bubbling-fluid pluralized bed is carefully understood and implemented in the design and layout of the gas distributors. Broadly speaking, the bed comprises of two zones—a dense bubbling zone, and a lean fluidizing zone (FIG. 4). The bubbling zone has a lower entrance zone that has a slightly decreased solids density due to the adjacent gas distributor, and a main zone of constant density. An increase in gas velocity results in a linear decrease in bed density, and a commensurate increase of the height of constant density zone.

A dense bubbling bed has regions of low solid density, sometimes called as gas pockets or voids. These regions are called bubble phase. The region of higher solid density is called the emulsion region or the dense phase. Within the dense phase, there is also an on-going solids circulation phenomena that is conventionally referred to as backmixing. Additionally, based upon the fluidization gas velocities, the bed may be operating in a bubbling, slugging or turbulent fluidization regime. Maximization of the backmixing phenomena is preferably attained under turbulent fluidization conditions.

At a certain height, the bubbling bed transitions into a lean fluidized zone of decreasing densities. There is minimal entrainment at the top of the lean fluidized zone and at a certain height the particulate entrainment becomes approximately constant. This is referred to as the transport disengaging height (TDH) and this is where the vessel exit is positioned. When an internal cyclone is used, the unit is placed below the TDH position and this results in an economy regarding the overall height and cost.

In practice, the gaseous reactant products leaving the top of the fluid pluralized bed are directed into a disengaging zone to separate the catalyst fines from the gases. In one embodiment, one or more cyclones are located below the TDH in the upper portion of the reactor. The cyclones are equipped with diplegs with the leg of the primary cyclone dropping into the bottom section of the fluid pluralized bed and the leg of the secondary or fine cyclone dropping into an area of the fluid pluralized bed above the prior dipleg.

Other embodiments for particulate separation may also be satisfactorily utilized. These embodiments include the use of blow back filters, either internal to the reactor or external. Other embodiments include increasing the height of the reactor and various other methods including meshes, plates, etc. In all cases, the fines separated by an appropriate embodiment should be directed back into the fluidized catalyst section.

Fluidization Parameters

Particle size is an important property that contributes to appropriate fluidization and appropriate backmixing of the catalyst within the designated reactor bed/section. In one embodiment of the invention, the catalyst bed includes catalyst particles having a particle size (i.e., average diameter) of from 20 to 300 microns. Preferably, the catalyst particles have a particle size of from 50 to 200 microns.

Superficial gas velocity (SGV) is a measurement of the gas flowing through the catalyst bed. It is defined as:

$$\text{Superficial gas velocity (m/sec)} = \frac{\text{Volumetric flow rate of gases leaving the reactor (m}^3\text{/sec)}}{\text{Average cross section area of the reactor (m}^2\text{)}}$$

Typically, the fluid pluralized bed reactor SGV ranges from 0.1 msec to 2.0 msec. Low SGV may result in lack of fluidization while a high SGV may convert a dense phase fluid pluralized bed into a lean phase fluid pluralized bed where the voidage becomes so excessive that it inhibits contact between the catalyst and the reactive gases resulting in significant reaction yield loss.

In one embodiment, the SGV is not greater than 1.5 msec and in another not greater than 1.25 msec. Preferably, the reactor is maintained at a SGV of 0.3 msec to 1 msec and more preferably from 0.3 msec to 0.5 msec.

Particle density is also a significant contributor in the maintenance of fluid pluralized beds. It is calculated by using the following equation.

$$\rho_p = \frac{1}{1/\rho_s + V_p} [g/cm^3]$$

$\rho_s$: the true density of the substance constituting the particles (g/cm$^3$)
$V_p$: the pore volume (cm$^3$/g)
$\rho_p$: the particle density (g/cm$^3$)

A good range for particle density in this reactor is 1.5 g/cm$^3$ to 3 g/cm$^3$.

If the particle density is more than 3 g/cm$^3$, the bed will require extremely high gas flow rates to attain a fluidized condition. Such high gas flow rates will result in low per pass conversions because the volumetric hourly space velocity will become excessive.

If the particle density is less than 1.5 g/cm$^3$, there will be a significant excess of catalyst going off into the lean phase and a small amount in the dense reactive phase. A lot of the catalyst will flow into the upper section and put a heavy burden on the cyclones and diplegs. It is possible that the catalyst layer will swell up at relatively low superficial linear velocities and flood the reactor.

Bed density is another criteria that has to be carefully considered. The bed density of the reactor is defined as the volume fraction of catalyst solids in the reactor. Generally, the catalyst in the dense phase is maintained at a solids volume fraction ranging from 0.25 to 0.6. This fraction translates to 25% to 60% of the volume in the bed is occupied by the solid catalyst particles. In the lean phase, which is above the dense phase zone, the solids void fraction typically ranges from 0.15 to 0.3, which translates into 15 to 30% volume in the bed occupied by the solid catalyst particles. Preferably, the catalyst in the dense phase is maintained at a solids volume fraction ranging from 0.4 to 0.5 and in the lean phase, the catalyst is maintained at a solids volume fraction ranging from 0.2 to 0.25.

Backmixing

Backmixing is a state in a reactor where the contents are well stirred and uniform in composition throughout. Consequently, the exit stream leaving this reactor should have the same composition as the fluid within the reactor.

Backmixing of the catalyst in this application is typically attained by utilizing proper reactor design and a combination of superficial gas velocities, aspect ratio of the catalyst bed and the catalyst particle size and density. The flow gas through the dense phase zone is adequate to keep the catalyst in the dense phase zone with sufficient backmixing. Good backmixing results in a remarkably temperature stable system without hot spots, making for a good control of the reaction. Further, the large gas solid contact area as well as good contacting of the solid-gas phases makes this an efficient system for effecting the catalytic reactions and heat transfer which achieve a low ΔT across the reactor, both radially and axially.

In addition to the proper superficial gas velocity, bed density and particle size and density as mentioned above, in order to achieve the proper level of backmixing in the dense phase bed, the aspect ratio of the catalyst bed should be kept relatively low. According to this invention, the aspect ratio is the ratio of the height of the catalyst bed to the diameter of the catalyst bed. Preferably, the dense phase bed is maintained at a catalyst bed height to diameter ratio of not greater than 10:1, more preferably not greater than 5:1, and most preferably not greater than about 2:1.

Distributors

Kinetics in the reactor is conducted by injecting the reactant gases through appropriate distributors. The function of the distributors is to evenly distribute the reactant gases so as to fluidize the catalyst in the reactor in such a way as to maintain sufficient backmix capabilities.

There may be several distributors axially positioned approaching a logarithmic distribution along the fluid pluralized bed reactor. A reactor, for example, may typically be equipped with three distributors, one at the bottom, one at position x and one at position 10x, where x is an arbitrary axial dimension. Each distributor then generates its own fluidization characteristic along with its own backmix envelope.

Each one of the backmix envelopes that has been developed will have its independent kinetics, the commensurate heat release (these reactions are highly exothermic) and volume contraction (the overall DME synthesis reaction converts three moles of CO plus three moles of $H_2$ into one mole of DME and one mole of $CO_2$). The temperature increase within the backmix envelope along with a volumetric decrease of gas creates issues with regards to fluidization and backmix.

It has been discovered that introducing the gas through the distributors and into the reactor must be done under a temperature control algorithm where temperature sensors located in the bed directly above the distributors control the amount and the temperature of the reactant gas. The backmix characteristics of the fluid pluralized bed are normally analyzed by embedding several temperature sensors within the bed and looking at the temperature differences between the sensors. Ideally a good backmix system will exhibit the temperature differences to be approaching zero.

Figure 5:
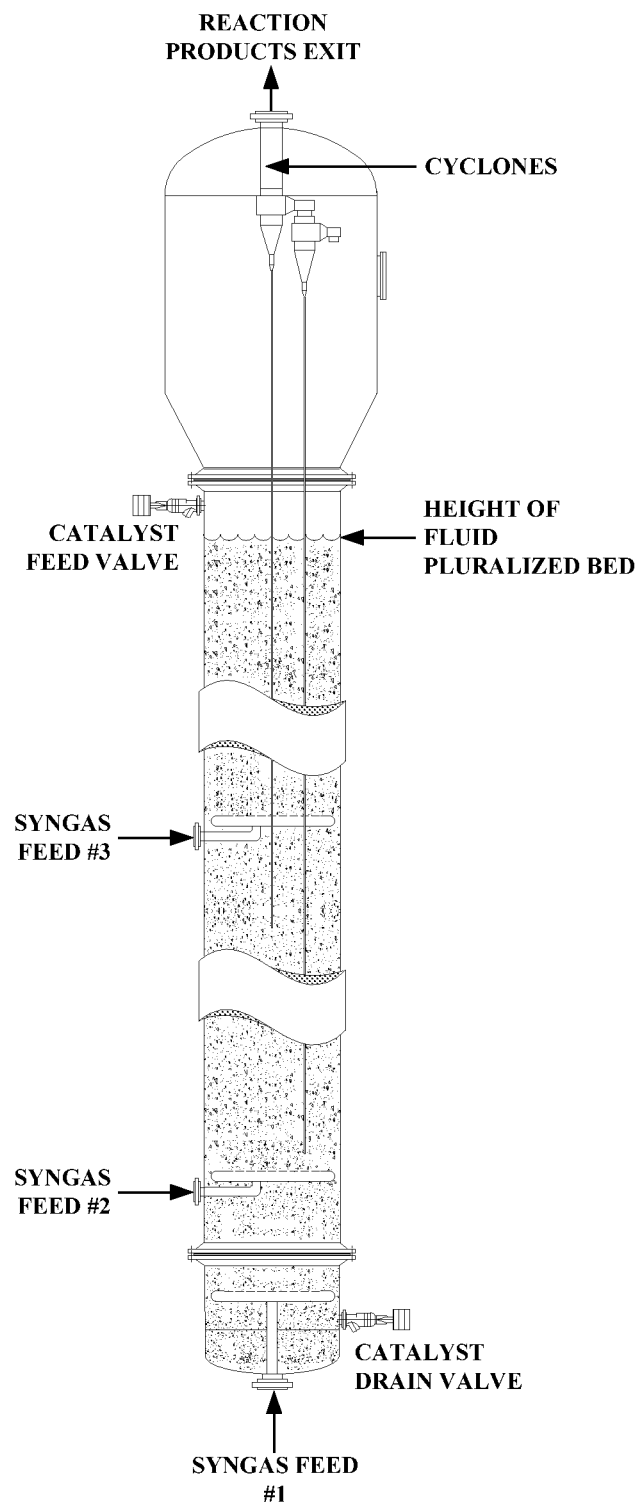
FIG. 5 is a proposed fluid pluralized bed reactor equipped with three distributors.

The proposed reactor is equipped with three distributors as shown in FIG. 5. In one embodiment of the reactor, the reactant gases enter at three sections: one at the bottom of the reactor through a distributor and two entries are along the side of the reactor at different heights. These three gas entries through their distributors result in three independent yet linked backmix reactors where the temperature is controlled not only by the temperatures of the feed gases but also by limiting the conversion of the reactants. It is obvious that these gas flow rates will also be a determinating factor of the reaction completion. Because of the highly exothermic nature of the overall reaction, it is sometimes important to control the overall mole conversion of the CO in a range from 25% to 60%. Preferably, conversions are maintained in the range from 30% to 55% and more preferably from 40% to 50%.

The fluid pluralized bed reactor is proposed as the ideal device for DME synthesis. Compared with the slurry reactor, the gas-solid mass transfer resistance in a fluid pluralized bed reactor is so small that it can be neglected, and excellent temperature control is also achievable due to the vigorous mixing of catalyst particles in the bed. Almost all of the reactions occur in the dense phase, which contains the catalyst particles, whereas the bubble phase does not contribute significantly to the reaction due to low solid concentration. Concentration gradients are established between the two phases, due to the depletion of reactants and the synthesis of products, inducing the diffusion of products from the dense phase to the bubble phase, and that of the reactants in the opposite direction.

The syngas-to-DME process is highly exothermic. A critical factor for DME reactor design is the management of the heat released by the reactions. The heat released by DME production can generate 2.4 tons of steam per ton of DME, equivalent to an adiabatic temperature rise of about 1,000° C. (1,832° F.) at a complete conversion of syngas with a 1:1 molar ratio of $H_2$:CO in the feed gas. The problem is especially significant as the catalyst of DME synthesis may be deactivated rapidly when the temperature is over 280° C. (536° F.).

It has shown that fluid bed technology is more efficient for DME synthesis than slurry reactor and fixed bed technologies. When H2/CO molar ratio equals 1.0 in the feed gas, the CO conversion and DME selectivity are 48.5% and 97% in a fluid bed reactor, compared to the values of 17% and 70% in a slurry reactor under the same conditions, and to 10.7% and 91.9% in a fixed bed reactor under its normal conditions. The superior efficiency of the fluid bed results from the elimination of diffusional limitations, giving rise to an effectiveness factor very close to one, and also because of the shift of equilibrium to more favorable conditions, such as the product diffusion from the dense phase to the bubble phase.

The sensitivity simulation shows that, the effect of the mass transfer coefficient can be ignored, the optimum $H_2$/CO molar ratio in the make-up syngas is between 0.9 to 1.1 while in the feed gas (make-up syngas plus recycle syngas) to the DME reactor is between 0.9 to 1.5. The enhancement of pressure improves DME productivity substantially. High temperature is also favorable for DME synthesis up to a maximum temperature of 285° C. (545° F.), past which it starts dropping gradually.

The direct conversion of the equimolar H2 and CO gas mixture in the make-up syngas into DME is an extremely exothermic reaction. In view of this, our reactor has been specially designed to maintain a highly isothermal profile. The DME catalyst is susceptible to rapid coking in case the operating conditions are upset for some unforeseen reason(s), therefore it's essential that the catalyst can be added or replaced with a minimum of difficulty and effort.

DME Fluid Pluralized Bed Reactor

The fluid pluralized bed reactor is configured to ensure that the heat generated within the reactor during the syngas to DME conversion reaction is balanced by the heat needed to bring the feed gases up to the desired temperature either with or without the internal heat transmission tube in the reactor.

The kinetics of the reactions are such that the bulk of the reactions is typically completed within a short distance downstream of the entry of the feed gases. In order to spread the reaction kinetics in a more isothermal fashion, it is convenient and appropriate to be able to introduce the feed gases in controlled quantities at several sections along the reactor. The feed gases in that case serve to also quench the reactor temperatures and bring them somewhat closer to an isothermal mode.

Each gas quench section also generates an environment of backmixing of catalyst solids that effectively distributes the heat generated uniformly throughout the bed. The circulating pattern of the catalyst lifts the catalyst upwards initially, picking up heat of reactions. This catalyst then circulates downwards to meet the fresh feed gases and preheat them quickly to reaction temperatures. The deployment of catalyst solids in this fashion greatly simplifies the kinetics and reduces or eliminates the amount of overall heat transfer surface area needed to control the process.

Appropriate injection of quenched recycle syngas into different sections along the reactor then creates a series of independent, yet connected, backmix environments for optimizing the reactions and isothermality. In each section, temperature management can further be conducted by controlling the incoming temperature of the make-up syngas—whether they need to be cooled or warmed is a function of the catalyst. In one embodiment of the invention, the fluid pluralized bed reactor is maintained at a temperature ranging from 150° C. to 350° C. (302° F. to 662° F.). Preferably, it is maintained at a temperature of 180° C. to 320° C. (356° F. to 608° F.), more preferably from 200° C. to 280° C. (392° F. to 536° F.).

In one embodiment, the temperature of the fluid pluralized bed is maintained by controlling the temperature of the feed gases entering the reactor through the reactor bottom gas distributor. In another embodiment, the feed gases may be entering the reactor at several different sections. The temperatures of the different incoming feed gas streams may be independently controlled to generate axial isothermality of the reactor. Preferably, the make-up syngas stream flowing into the reactor enters at ambient temperature, 37.8° C. (100.0° F.) while the recycle syngas enters at methanol absorber outlet temperatures ranging from −21° C. to −5° C. (−6° F. to 23° F.).

The treated gas from the methanol absorber contains unconverted syngas. In order to maximize the production of DME, this gas needs to be recycled around the DME synthesis loop. A small amount of the recycle gas is purged in order to remove the accumulating inert gases in the loop.

Crude DME Production

The effluent from the reactor is cooled to 14° F. to condense out most of the water and methanol and part of the DME product. The remaining of the DME product and most of the acid gas ($CO_2$) in the vapor phase is removed by an absorber using methanol as the absorption solvent. The typical stream descriptions of the condensate from the condenser and rich solvent from methanol absorber are shown below (Table 3):

TABLE 3

Typical Crude DME Product

| | Stream | |
|---|---|---|
| | Condensate from the Condenser | Rich Solvent from Methanol Absorber |
| Phase | Liquid | Liquid |
| Temp., °F. | 14.0 | 35.1 |
| Pressure, psig | 710.5 | 710.5 |
| Composition, mole % | | |
| $CH_4$ | 2.80 | 0.71 |
| $CO_2$ | 18.52 | 8.08 |
| $N_2$ | 0.34 | 632 PPM |
| $H_2O$ | 5.95 | 0.14 |
| CO | 0.75 | 0.14 |
| $H_2$ | 0.59 | 0.14 |
| $CH_4O$ | 18.70 | 85.92 |
| DME | 52.35 | 4.81 |
| TOTAL | 100.00 | 100.00 |

The typical treated gas (Table 4) from the methanol absorber contains unconverted syngas. In order to maximize the production of DME, this gas needs to be recycled around the DME synthesis loop. A small amount of the recirculating gas is purged in order to remove the accumulating inert gases in the loop.

TABLE 4

Typical Treated Recycle Gas

| Component | Mole % |
|---|---|
| Methane | 19.78 |
| Carbon Monoxide | 22.07 |
| Carbon Dioxide | 5.97 |
| Water | 1 PPM |
| Hydrogen | 40.76 |
| Oxygen | 0.00 |
| Nitrogen | 11.30 |
| Methanol | 897 PPM |
| DME | 351 PPM |
| TOTAL | 100.00 |

Hydrogen Recovery Via PSA Unit

About 75% of the hydrogen content in the purge gas of the DME synthesis loop can be recovered via a PSA unit. Control of PSA sequencing will be by a dual redundant PLC.

Product Hydrogen Quality

The required purity of product hydrogen from the PSA units is:

| Hydrogen Content | 99.9 mole % (dry basis) (min) Excluding $N_2$ |
|---|---|
| $CO + CO_2$ | <10 ppmv |
| Nitrogen | Not significantly removed |

To ensure fast and effective optimization of the PSA Unit on start-up, it is essential that on-line, continuous product analysis be installed. This may take the form of a simple thermal conductivity unit measuring just hydrogen purity in the range 98 to 100 mole %. However, this type of analyzer is not capable of measuring individual component impurity levels and since this is important to the operation of downstream equipment, alternate and/or additional analysis systems should be added.

Absorbents

The Pressure Swing Adsorption System described in this application requires the use of more than one adsorbent.

The adsorbents will comprise of:

Molecular sieve
Activated Carbon
Activated alumina

Purification

The light end in the stream of condensate from the condenser is removed by light end distillation column 1, and the crude DME is purified by DME distillation column 1 (Table 5):

TABLE 5

Typical Fuel Grade DME Product and Recycled Crude Methanol

| | Stream | |
|---|---|---|
| | DME Product | Methanol & Water |
| Phase | Liquid | Liquid |
| Temp., °F. | 96.4 | 264.4 |
| Pressure, psig | 101.3 | 101.3 |
| Composition, mole % | | |
| $CH_4$ | 0.00 | 0.00 |
| $CO_2$ | 81 PPM | 0.00 |
| $N_2$ | 0.00 | 0.00 |
| $H_2O$ | 46 PPM | 24.12 |
| CO | 0.00 | 0.00 |
| $H_2$ | 0.00 | 0.00 |
| $CH_4O$ | 0.00 | 75.88 |
| DME | 99.99 | 0.00 |
| TOTAL | 100.00 | 100.00 |

The methanol & water stream obtained from the bottom of the distillation column is recycled to the DME fluid pluralized bed reactor.

Similarly, the light end in the stream of rich solvent from the methanol absorber is removed by light end distillation column 2, and the crude DME is purified by DME distillation column 2 (Table 6):

TABLE 6

Typical Fuel Grade DME Product and Regenerated Absorption Solvent

| | Stream | |
|---|---|---|
| | DME Product | Absorption Solvent |
| Phase | Liquid | Liquid |
| Temp., °F. | 96.4 | 260.1 |
| Pressure, psig | 101.3 | 101.3 |
| Composition, mole % | | |
| $CH_4$ | 0.00 | 0.00 |
| $CO_2$ | 43 PPM | 0.00 |
| $N_2$ | 0.00 | 0.00 |
| $H_2O$ | 0.00 | 0.16 |
| CO | 0.00 | 0.00 |
| $H_2$ | 0.00 | 0.00 |
| $CH_4O$ | 7 PPM | 99.71 |
| DME | 99.99 | 0.13 |
| TOTAL | 100.00 | 100.00 |

The absorption solvent thus regenerated is recycled to the methanol absorber for reuse. The DME produced from these two DME distillation columns has a purity greater than 99.98 mol % which is suitable for fuel grade DME applications.

Figure 6:
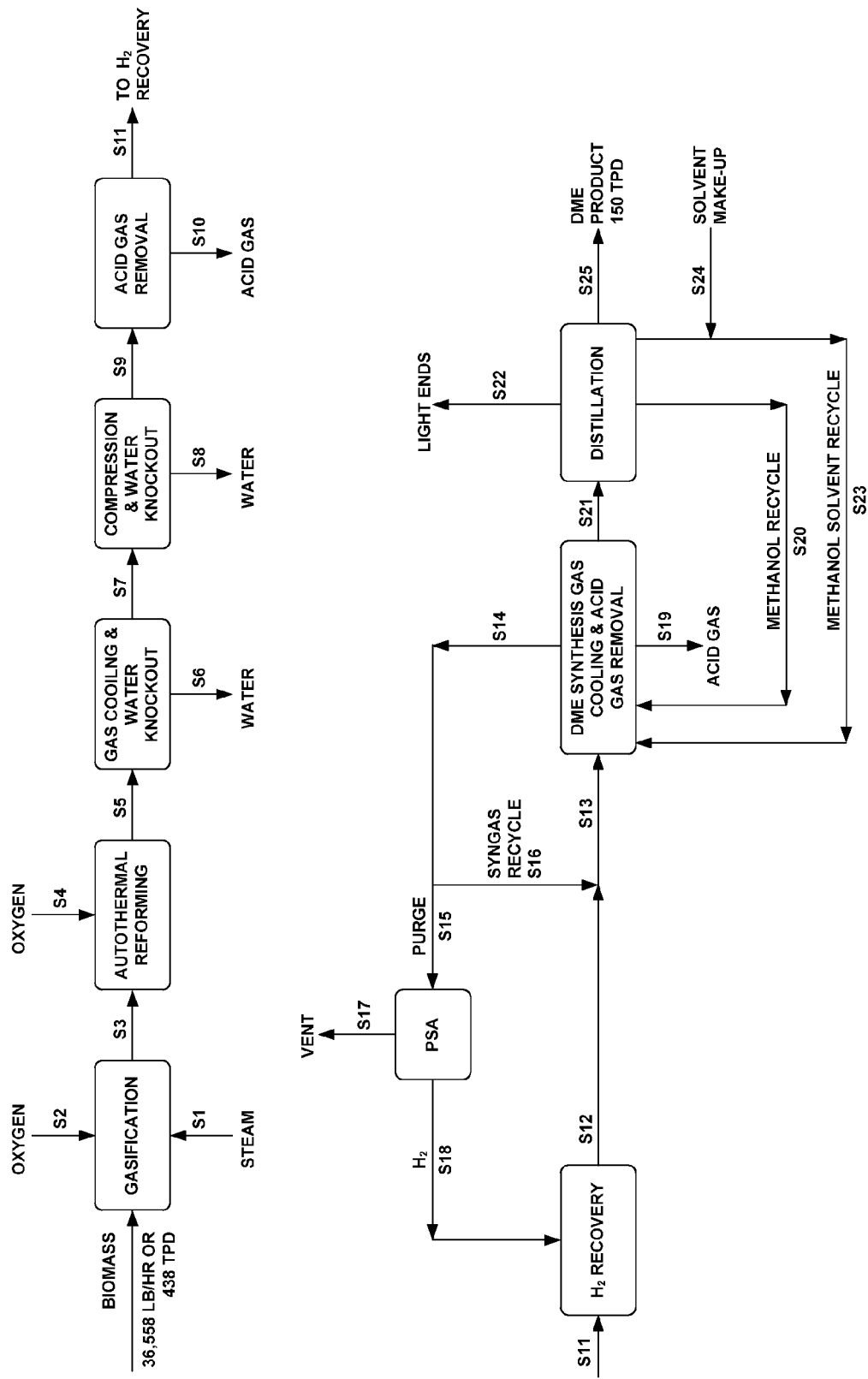
FIG. 6 is a simplified process flow block diagram for the production of 150 tons/day of fuel grade DME from biomass.

A simplified process flow block diagram for the production of 150 tons/day of fuel grade DME from biomass is shown in FIG. 6. The details of this application will be illustrated in Example 1. This process was simulated using Aspen Plus Version 7.1. The corresponding stream description is shown in Table 7.

Figure 7:
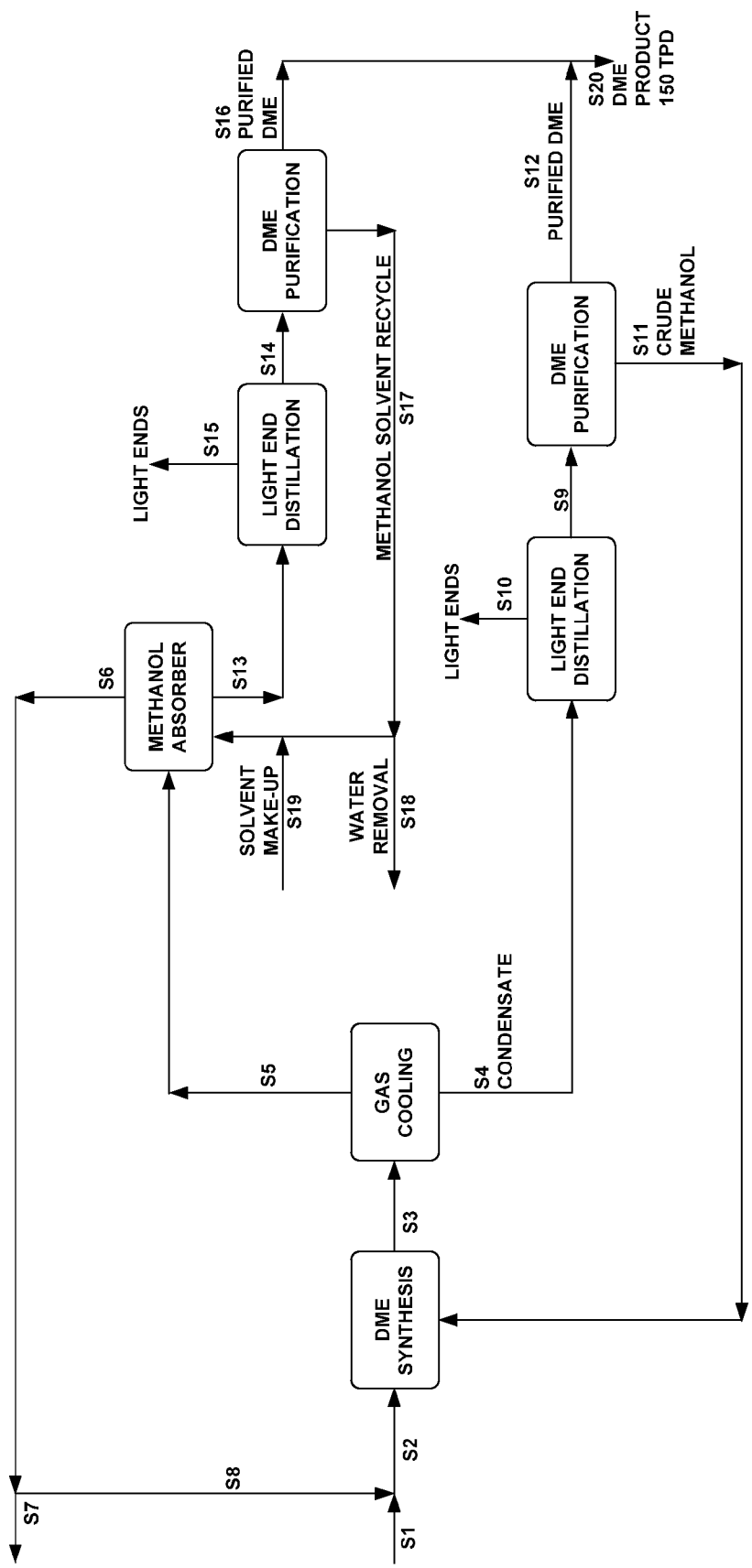
FIG. 7 is a detailed process flow block diagram for the DME synthesis, gas cooling, acid gas removal and DME purification sections.

A detailed process flow block diagram for the DME synthesis, gas cooling, acid gas removal and DME purification sections is shown in FIG. 7 and its corresponding stream description in Table 8.

TABLE 7

150 TPD DME PLANT

| | Stream No. | | | | | | | |
|---|---|---|---|---|---|---|---|---|
| | S1 | S2 | S3 | S4 | S5 | S6 | S7 | S8 |
| Phase | V | V | V | V | V | L | V | L |
| Temperature ° F. | 800 | 350 | 1750 | 350 | 1557 | 108 | 108 | 108 |
| Pressure, psig | 150 | 150 | 150 | 150 | 144 | 135 | 135 | 284 |
| Flowrate, #mol/hr | 238.5294 | 394.4257 | 2423.1599 | 29.0630 | 2637.6238 | 386.3010 | 2251.3236 | 12.4345 |
| Composition, mol % | | | | | | | | |
| $CH_4$ | 0.0000 | 0.0000 | 6.5902 | 0.0000 | 1.9992 | 0.0000 | 2.3423 | 0.0000 |
| $CO_2$ | 0.0000 | 0.0000 | 16.3313 | 0.0000 | 14.7950 | 0.0000 | 17.3311 | 0.0000 |
| $N_2$ | 0.0000 | 2.0000 | 0.3540 | 2.0000 | 0.3466 | 0.0000 | 0.4060 | 0.0000 |
| $O_2$ | 0.0000 | 98.0000 | 0.0000 | 98.0000 | 0.0000 | 0.0000 | 0.0000 | 0.0000 |
| $H_2O$ | 100.0000 | 0.0000 | 18.4786 | 0.0000 | 15.2890 | 100.0000 | 0.7563 | 100.0000 |
| CO | 0.0000 | 0.0000 | 32.9540 | 0.0000 | 34.5381 | 0.0000 | 40.4644 | 0.0000 |
| $H_2$ | 0.0000 | 0.0000 | 25.2792 | 0.0000 | 33.0191 | 0.0000 | 38.6847 | 0.0000 |
| $H_2S$ | 0.0000 | 0.0000 | 99 PPM | 0.0000 | 91 PPM | 0.0000 | 106 PPM | 0.0000 |
| COS | 0.0000 | 0.0000 | 4 PPM | 0.0000 | 4 PPM | 0.0000 | 5 PPM | 0.0000 |
| $NH_3$ | 0.0000 | 0.0000 | 23 PPM | 0.0000 | 35 PPM | 0.0000 | 41 PPM | 0.0000 |
| $CH_4O$ | 0.0000 | 0.0000 | 0.0000 | 0.0000 | 0.0000 | 0.0000 | 0.0000 | 0.0000 |
| DME | 0.0000 | 0.0000 | 0.0000 | 0.0000 | 0.0000 | 0.0000 | 0.0000 | 0.0000 |

| | Stream No. | | | | | | | |
|---|---|---|---|---|---|---|---|---|
| | S9 | S10 | S11 | S12 | S13 | S14 | S15 | S16 |
| Phase | V | V | V | V | V | V | V | V |
| Temperature ° F. | 108 | 114 | 108 | 100 | 48 | 23 | 23 | 23 |
| Pressure, psig | 711 | 0 | 710 | 710 | 710 | 710 | 710 | 710 |
| Flowrate, #mol/hr | 2238.8948 | 487.2304 | 1751.4422 | 1766.3551 | 5302.6448 | 3585.0645 | 48.7748 | 3536.2897 |
| Composition, mol % | | | | | | | | |
| $CH_4$ | 2.3553 | 2.6506 | 2.2734 | 2.2543 | 13.9408 | 19.7783 | 19.7783 | 19.7783 |
| $CO_2$ | 17.4271 | 70.3783 | 2.6969 | 2.6741 | 4.8734 | 5.9716 | 5.9716 | 5.9716 |
| $N_2$ | 0.4083 | 0.1511 | 0.4799 | 0.4758 | 7.6955 | 11.3021 | 11.3021 | 11.3021 |
| $O_2$ | 0.0000 | 0.0000 | 0.0000 | 0.0000 | 0.0000 | 0.0000 | 0.0000 | 0.0000 |
| $H_2O$ | 0.2054 | 0.8406 | 197 PPM | 196 PPM | 66 PPM | 1 PPM | 1 PPM | 1 PPM |
| CO | 40.6891 | 16.3485 | 47.4655 | 47.0649 | 30.3942 | 22.0670 | 22.0670 | 22.0670 |
| $H_2$ | 38.8996 | 9.5661 | 47.0646 | 47.5114 | 43.0062 | 40.7562 | 40.7562 | 40.7562 |
| $H_2S$ | 107 PPM | 452 PPM | 0.0000 | 0.0000 | 0.0000 | 0.0000 | 0.0000 | 0.0000 |
| COS | 5 PPM | 22 PPM | 0.0000 | 0.0000 | 0.0000 | 0.0000 | 0.0000 | 0.0000 |
| $NH_3$ | 41 PPM | 173 PPM | 0.0000 | 0.0000 | 0.0000 | 0.0000 | 0.0000 | 0.0000 |
| $CH_4O$ | 0.0000 | 0.0000 | 0.0000 | 0.0000 | 598 PPM | 897 PPM | 897 PPM | 0.0000 |
| DME | 0.0000 | 0.0000 | 0.0000 | 0.0000 | 234 PPM | 351 PPM | 351 PPM | 0.0000 |

| | Stream No. | | | | | | | |
|---|---|---|---|---|---|---|---|---|
| | S17 | S18 | S19 | S20 | S21 | S22 | S23 | S24 | S25 |
| Phase | V | V | V | L | V + L | V | L | L | L |
| Temperature ° F. | 23 | 23 | −56 | 100 | 33 | −51 | 260 | 14 | 96 |
| Pressure, psig | 710 | 710 | 101 | 710 | 101 | 101 | 101 | 710 | 101 |
| Flowate, #mol/hr | 33.8657 | 14.9091 | 313.0383 | 52.7272 | 3639.1756 | 49.3894 | 2953.0180 | 1.9730 | 271.3786 |
| Composition, mol % | | | | | | | | | |
| $CH_4$ | 28.4855 | 0.0000 | 7.7423 | 0.0000 | 0.8293 | 12.0315 | 0.0000 | 0.0000 | 0.0000 |
| $CO_2$ | 8.6005 | 0.0000 | 88.4006 | 0.0000 | 8.6854 | 79.6639 | 0.0000 | 0.0000 | 2 PPM |
| $N_2$ | 16.2778 | 0.0000 | 0.6918 | 0.0000 | 792 PPM | 1.4569 | 0.0000 | 0.0000 | 0.0000 |
| $O_2$ | 0.0000 | 0.0000 | 0.0000 | 0.0000 | 0.0000 | 0.0000 | 0.0000 | 0.0000 | 0.0000 |
| $H_2O$ | 1 PPM | 0.0000 | 0.0000 | 23.9567 | 0.4796 | 0.0000 | 0.1633 | 0.0000 | 12 PPM |
| CO | 31.7818 | 0.0000 | 1.5272 | 0.0000 | 0.1749 | 3.2056 | 0.0000 | 0.0000 | 0.0000 |
| $H_2$ | 14.6747 | 100.0000 | 1.5429 | 0.0000 | 0.1673 | 2.5451 | 0.0000 | 0.0000 | 0.0000 |
| $H_2S$ | 0.0000 | 0.0000 | 0.0000 | 0.0000 | 0.0000 | 0.0000 | 0.0000 | 0.0000 | 0.0000 |

TABLE 7-continued

150 TPD DME PLANT

| COS | 0.0000 | 0.0000 | 0.0000 | 0.0000 | 0.0000 | 0.0000 | 0.0000 | 0.0000 | 0.0000 |
|---|---|---|---|---|---|---|---|---|---|
| $NH_3$ | 0.0000 | 0.0000 | 0.0000 | 0.0000 | 0.0000 | 0.0000 | 0.0000 | 0.0000 | 0.0000 |
| $CH_4O$ | 0.1292 | 0.0000 | 0.0000 | 75.3623 | 81.9971 | 0.0000 | 99.7043 | 100.0000 | 4 PPM |
| DME | 505 PPM | 0.0000 | 953 PPM | 0.6810 | 7.5873 | 1.0972 | 0.1324 | 0.0000 | 99.9982 |

TABLE 8

150 TPD DME PLANT

| | Stream No. | | | | | | | | | |
|---|---|---|---|---|---|---|---|---|---|---|
| | S1 | S2 | S3 | S4 | S5 | S6 | S7 | S8 | S9 | S10 |
| Phase | V | V | V | L | V | V | V | V | L | V |
| Temperature ° F. | 100 | 48 | 500 | 14 | 14 | 23 | 23 | 23 | 116 | −51 |
| Pressure, psig | 710 | 710 | 710 | 710 | 710 | 710 | 710 | 710 | 101 | 101 |
| Flowrate, #mol/hr | 1766.3551 | 5302.6448 | 4270.1830 | 212.4433 | 4057.6448 | 3585.0645 | 48.7748 | 3536.2897 | 163.0440 | 49.3894 |
| Composition, mol % | | | | | | | | | | |
| $CH_4$ | 2.2554 | 13.9408 | 17.3117 | 2.7974 | 18.0716 | 19.7783 | 19.7783 | 19.7783 | 0.0000 | 12.0315 |
| $CO_2$ | 2.6741 | 4.8734 | 12.4154 | 18.5221 | 12.0957 | 5.9716 | 5.9716 | 5.9716 | 3 PPM | 79.6639 |
| $N_2$ | 0.4758 | 7.6955 | 9.5563 | 0.3387 | 10.0389 | 11.3021 | 11.3021 | 11.3021 | 0.0000 | 1.4569 |
| $H_2O$ | 196 PPM | 66 PPM | 0.3177 | 5.9462 | 230 PPM | 1 PPM | 1 PPM | 1 PPM | 7.7478 | 0.0000 |
| CO | 47.0649 | 30.3942 | 18.6755 | 0.7453 | 19.6142 | 22.0670 | 22.0670 | 22.0670 | 0.0000 | 3.2056 |
| $H_2$ | 47.5114 | 43.0062 | 34.3597 | 0.5917 | 36.1277 | 40.7562 | 40.7562 | 40.7562 | 0.0000 | 2.5451 |
| $CH_4O$ | 0.0000 | 0.0000 | 0.9597 | 18.7045 | 306 PPM | 897 PPM | 897 PPM | 897 PPM | 24.3712 | 0.0000 |
| DME | 0.0000 | 0.0000 | 6.4040 | 52.3540 | 3.9983 | 351 PPM | 351 PPM | 351 PPM | 67.8806 | 1.0972 |

| | Stream No. | | | | | | | | | |
|---|---|---|---|---|---|---|---|---|---|---|
| | S11 | S12 | S13 | S14 | S15 | S16 | S17 | S18 | S19 | S20 |
| Phase | L | L | L | L | V | L | L | L | L | L |
| Temperature ° F. | 259 | 96 | 35 | 234 | −56 | 96 | 260 | 260 | 14 | 96 |
| Pressure, psig | 101 | 101 | 710 | 101 | 101 | 101 | 101 | 101 | 710 | 101 |
| Flowrate, #mol/hr | 52.7272 | 110.6786 | 3426.7323 | 3113.6980 | 313.0383 | 160.7000 | 2953.0180 | 0.9288 | 1.9730 | 271.3786 |
| Composition, mol % | | | | | | | | | | |
| $CH_4$ | 0.0000 | 0.0000 | 0.7073 | 0.0000 | 7.7423 | 0.0000 | 0.0000 | 0.0000 | 0.0000 | 0.0000 |
| $CO_2$ | 0.0000 | 5 PPM | 8.0756 | 0.0000 | 88.4006 | 0.0000 | 0.0000 | 0.0000 | 0.0000 | 2 PPM |
| $N_2$ | 0.0000 | 0.0000 | 632 PPM | 0.0000 | 0.6918 | 0.0000 | 0.0000 | 0.0000 | 0.0000 | 0.0000 |
| $H_2O$ | 23.9567 | 29 PPM | 0.1407 | 0.1549 | 0.0000 | 0.0000 | 0.1633 | 100.0000 | 0.0000 | 12 PPM |
| CO | 0.0000 | 0.0000 | 0.1395 | 0.0000 | 1.5272 | 0.0000 | 0.0000 | 0.0000 | 0.0000 | 0.0000 |
| $H_2$ | 0.0000 | 0.0000 | 0.1409 | 0.0000 | 1.5429 | 0.0000 | 0.0000 | 0.0000 | 0.0000 | 0.0000 |
| $CH_4O$ | 75.3623 | 0.0000 | 85.9209 | 94.5590 | 0.0000 | 7 PPM | 99.7043 | 0.0000 | 100.0000 | 4 PPM |
| DME | 0.6810 | 99.9966 | 4.8119 | 5.2861 | 953 PPM | 99.9992 | 0.1324 | 0.0000 | 0.0000 | 99.9982 |

Catalyst

This invention uses an attrition resistant bifunctional catalyst where methanol synthesis-water gas shift reaction is one function and the methanol dehydration to DME reaction is the other function.

The procedure to manufacture of this catalyst comprises the following steps:
  (a) co-precipitation preparation of $CuCO_3$, $ZnCO_3$, $CrO_2$ and $La_2(CO_3)_3$ using reagents of $Cu(NO_3)_2$, $Zn(NO_3)_2$, $Cr(NO_3)_3$, $La(NO_3)_3$ and $Na_2CO_3$ at 80° C. to a final pH value of 7, then $Al(OH)_3$ powder was added to the co-precipitate,
  (b) preparation of a slurry with the dehydrogenation component HZSM-5 or SUZ-4,
  (c) addition of silica sol as binder with a particle size less than 15 nm and a pH value of 4-5 into the slurry,
  (d) spray drying the slurry to form microspheres and
  (e) calcination.

The catalyst comprises of particles having a size ranging from 20 to 300 μm and is optimized for fluid pluralized bed reactor operation.

The following examples provide data for the balancing of the heat generates within the fluid pluralized bed reactor during the syngas to DME synthesis against the heat needed to bring the make-up syngas and recycle gas up to the desired DME reaction temperature, i.e. 260° C. to 280° C. (500° F. to 536° F.) either with or without the internal heat transmission tube in the reactor. Two different absorption solvents for the removal of the acid gases generated in the DME synthesis loop were evaluated. Other options include the use of a water gas shift reactor after the autothermal reformer and the recycle of the whole DME synthesis loop purge gas to the autothermal reformer were also investigated. Finally, the pressure of the two light end columns is changed to three different pressure levels: 224.6 psig (16 bar), 347.9 psig (25 bar) and 463.9 psig (33 bar) in order to increase the condenser temperature. All the examples are given by way of illustration only and not by way of limitation to the present invention.

EXAMPLE 1

36,358 lb/hr of biomass with the composition shown below is fed to a gasifier operated at 1750° F. and 150 psig.

| Biomass Proximate Analyses | |
|---|---|
| Comp. | Wt % |
| Moisture | 10.000 |
| Fixed Carbon | 11.954 |
| Volatiles | 83.400 |
| Ash | 4.646 |
| Total | 110.000 |

| Biomass Ultimate Analyses | |
|---|---|
| Comp. | Wt % |
| Carbon | 49.454 |
| Hydrogen | 5.755 |
| Nitrogen | 0.061 |
| Sulfur | 0.024 |
| Oxygen | 40.060 |
| Ash | 4.646 |
| Total | 100.000 |

An oxidative autothermal reformer operated at 1557° F. and 144 psig is provided for the simultaneous removal of tars, benzene/toluene/xylene components, and for decreasing methane concentration by reforming while optimizing energy efficiency. A syngas with the composition below is obtained:

| Syngas from Autothermal Reformer | |
|---|---|
| Phase | Vapor |
| Temp., ° F. | 1556.8 |
| Pressure, psig | 144.0 |
| Flowrate, lbmol/hr | 2637.25 |
| $H_2/CO$, Molar Ratio | 0.9560 |
| Composition | Mol % |
| $CH_4$ | 2.00 |
| $CO_2$ | 14.80 |
| $N_2$ | 0.35 |
| $H_2O$ | 15.29 |
| CO | 34.54 |
| $H_2$ | 33.02 |

The gas is then cooled down to 108° F. to knock out most of its moisture content before it is compressed by a two-stage compressor with intercooler, aftercooler and water knockout to 710 psig.

The compressed syngas is then passed through an absorber using $CH_3$—O—(—$CH_2$—$CH_2$—O)$_5$—$CH_3$ ($C_{12}H_{26}O_6$) as the absorption solvent to remove 88 mol % of the $CO_2$ in the stream. The rich solvent is regenerated by a simple flash, and no thermal energy is required. The lean gas from the absorber is combined with $H_2$ recovered from the DME synthesis loop purge gas before it is fed to a DME fluid pluralized bed reactor. Part of the heat released by the exothermic reactions (Q=−10.48×10$^6$ Btu/hr) is removed by passing a heat transfer medium through a heat transmission tube in the fluid pluralized bed. This make-up syngas having the following composition is introduced through the distributor located at the bottom of the fluid pluralized bed reactor.

| Make-up Syngas to DME Reactor | |
|---|---|
| Phase | Vapor |
| Temp., ° F. | 100.0 |
| Pressure, psig | 710.5 |
| Flowrate, lbmol/hr | 1766.36 |
| $H_2/CO$, Molar Ratio | 1.0095 |
| Composition | Mol % |
| $CH_4$ | 2.25 |
| $CO_2$ | 2.67 |
| $N_2$ | 0.48 |
| $H_2O$ | 0.02 |
| CO | 47.07 |
| $H_2$ | 47.51 |

Due to the efficient backmixing is maintained in the fluid pluralized bed, the fresh make-up syngas is preheated quickly to reaction temperatures. The cooled recycle gas after the purge is served as the two other entries along the side of the reactor at different heights in order to have additional control of the reaction temperatures.

The effluent from the reactor is cooled to 14° F. to condense out most of the water and methanol and about 40% of the DME product. The remaining of the DME product and most of the acid gas ($CO_2$) in the vapor phase is removed by an absorber using methanol as the absorption solvent. The stream descriptions of the condensate from the condenser and rich solvent from methanol absorber are shown below.

| Crude DME Product | | |
|---|---|---|
| | Stream | |
| | Condensate from the Condenser | Rich Solvent from Methanol Absorber |
| Phase | Liquid | Liquid |
| Temp., ° F. | 14.0 | 35.1 |
| Pressure, psig | 710.5 | 710.5 |
| Flowrate, lbmol/hr | 212.44 | 3426.74 |
| Component Flow, lbmol/hr | | |
| $CH_4$ | 5.94 | 24.24 |
| $CO_2$ | 39.35 | 276.73 |
| $N_2$ | 0.72 | 2.17 |
| $H_2O$ | 12.63 | 4.82 |
| CO | 1.58 | 4.78 |
| $H_2$ | 1.26 | 4.83 |
| $CH_4O$ | 39.73 | 2944.28 |
| DME | 111.22 | 164.89 |

The light end in the stream of condensate from the condenser is removed by light end distillation column 1 and the crude DME is purified by DME distillation column 1:

| Fuel Grade DME Product and Recycled Crude Methanol | | |
|---|---|---|
| Stream | DME Product | Absorption Solvent |
| Phase | Liquid | Liquid |
| Temp., ° F. | 96.4 | 260.1 |

-continued

Fuel Grade DME Product and Recycled Crude Methanol

| Stream | DME Product | Absorption Solvent |
|---|---|---|
| Pressure, psig | 101.3 | 101.3 |
| Flowrate, lbmol/hr | 160.70 | 2953.00 |
| Component Flow, lbmol/hr | | |
| $CH_4$ | 0.00 | 0.00 |
| $CO_2$ | 0.00 | 0.00 |
| $N_2$ | 0.00 | 0.00 |
| $H_2O$ | 0.00 | 4.82 |
| CO | 0.00 | 0.00 |
| $H_2$ | 0.00 | 0.00 |
| $CH_4O$ | 0.00 | 2944.28 |
| DME | 160.70 | 3.90 |

The absorption solvent thus regenerated is recycled to the methanol absorber for reuse. The DME produced (150 tons/day) from these two DME distillation columns has a purity greater than 99.98 mol % which is suitable for fuel grade DME applications.

A simplified process flow block diagram for the production of 150 tons/day of fuel grade DME from biomass is shown in FIG. 6. This process was simulated using Aspen Plus Version 7.1. The corresponding stream description is shown in Table 7.

A detailed process flow block diagram for the DME synthesis, gas cooling, acid gas removal and DME purification sections is shown in FIG. 7 and its corresponding stream description in Table 8.

EXAMPLE 2

Same as Example 1 except that the internal heat transmission tube in the fluid pluralized bed reactor is removed. A higher recycle rate (from 3536 lbmol/hr to 6363 lbmol/hr) in the DME synthesis loop is required to maintain the same effluent temperature of the DME reactor. This higher recycle rate is obtained by injecting more steam to the gasifier (from 239 lbmol/hr to 378 lbmol/hr). The $H_2/CO$ molar ratio in the feed syngas to the DME reactor also increases from 1.4149 to 2.8088 due to the water gas shift reaction:

Feed Gases to DME Reactor

| Feed Gas to DME Reactor | Example 1 | Example 2 |
|---|---|---|
| Phase | Vapor | Vapor |
| Temp., ° F. | 47.5 | 39.5 |
| Pressure, psig | 710.5 | 710.5 |
| Flowrate, lbmol/hr | 5302.72 | 8183.06 |
| $H_2$/CO Molar Ratio | 1.4149 | 2.8088 |
| Component Flow, mol % | | |
| $CH_4$ | 13.94 | 13.46 |
| $CO_2$ | 4.87 | 4.91 |
| $N_2$ | 7.70 | 5.89 |
| $H_2O$ | 0.00 | 0.00 |
| CO | 30.40 | 19.86 |
| $H_2$ | 43.01 | 55.79 |
| $CH_4O$ | 0.06 | 0.07 |
| DME | 0.02 | 0.02 |

The higher recycle rate in the DME synthesis loop also reduces the partial pressure of the DME product in the phase separator, only 0.715 mol % of the DME produced is condensed out in the DME reactor effluent condenser compared to 40.672 mol % in Example 1.

Condensate from the Phase Separator

| | Example 1 | Example 2 |
|---|---|---|
| Phase | Liquid | Liquid |
| Temp., ° F. | 14.0 | 14.0 |
| Pressure, psig | 710.5 | 710.5 |
| Flowrate, lbmol/hr | 212.44 | 79.86 |
| Component Flow, lbmol/hr | | |
| $CH_4$ | 5.94 | 0.07 |
| $CO_2$ | 39.35 | 2.02 |
| $N_2$ | 0.72 | 0.00 |
| $H_2O$ | 12.63 | 37.99 |
| CO | 1.58 | 0.01 |
| $H_2$ | 1.26 | 0.02 |
| $CH_4O$ | 39.74 | 37.78 |
| DME | 111.22 | 1.97 |

Therefore, a higher methanol solvent flowrate is needed in Example 2 for the methanol absorber to absorb the additional DME content in the recycle syngas, 3935 μmol/hr as compared to 2953 μmol/hr in Example 1.

The DME and most of the $CH_4O$ in the condensate from the condenser can be recovered by a distillation column and are recycled back to the DME reactor:

Recovered DME and $CH_4O$ Recycled to DME Reactor

| Phase | Vapor |
|---|---|
| Temp., ° F. | 100.0 |
| Pressure, psig | 710.5 |
| Flowrate, lbmol/hr | 38.00 |
| Component Flow, lbmol/hr | |
| $CH_4$ | 0.07 |
| $CO_2$ | 2.02 |
| $N_2$ | 0.00 |
| $H_2O$ | 2.05 |
| CO | 0.01 |
| $H_2$ | 0.02 |
| $CH_4O$ | 31.86 |
| DME | 1.97 |

The light end in the stream of rich solvent from the methanol absorber bottom is separated by a light end distillation column, and the crude DME is purified by the DME distillation column:

Fuel Grade DME Product & Regenerated Absorption Solvent

| Stream | DME Product | Absorption Solvent |
|---|---|---|
| Phase | Liquid | Liquid |
| Temp., ° F. | 96.5 | 260.3 |
| Pressure, psig | 101.3 | 101.3 |
| Flowrate, lbmol/hr | 271.40 | 3935.44 |
| Component Flow, lbmol/hr | | |
| $CH_4$ | 0.00 | 0.00 |
| $CO_2$ | 0.01 | 0.00 |
| $N_2$ | 0.00 | 0.00 |
| $H_2O$ | 0.00 | 3.46 |
| CO | 0.00 | 0.00 |
| $H_2$ | 0.00 | 0.00 |
| $CH_4O$ | 0.00 | 3928.38 |
| DME | 271.39 | 3.60 |

In this example, all the DME is produced from a single DME distillation column. The absorption solvent thus regenerated at the column bottom is recycled to the methanol absorber for reuse.

EXAMPLE 3

Same as Example 2 except that the absorption solvent in the methanol absorber is replaced by $CH_3-O-(-CH_2-CH_2-O)_5-CH_3$ ($C_{12}H_{26}O_6$). Due to the higher solubility of the syngas in $C_{12}H_{26}O_6$, more biomass, oxygen and steam are required to produce the same amount of DME product:

| Rich Solvent from Methanol/$C_{12}H_{26}O_6$ Absorber | | | |
|---|---|---|---|
| Rich Solvent from Methanol/$C_{12}H_{26}O_6$ Absorber | Example 1 | Example 2 | Example 2 |
| Phase | Liquid | Liquid | Liquid |
| Temp., °F. | 35.1 | 34.3 | 32.0 |
| Pressure, psig | 710.5 | 710.5 | 710.5 |
| Flowrate, lbmol/hr | 3426.74 | 4533.33 | 2358.64 |
| Flowrate, lb/hr | 114,796 | 151,721 | 479,062 |
| Wt Ratio, wt % | 23.96 | 31.67 | 100.00 |
| Component Flow, lbmol/hr | | | |
| $CH_4$ | 24.24 | 27.92 | 38.16 |
| $CO_2$ | 276.73 | 283.49 | 280.64 |
| $N_2$ | 2.17 | 1.93 | 5.03 |
| $H_2O$ | 4.82 | 3.46 | 0.71 |
| CO | 4.78 | 3.83 | 17.11 |
| $H_2$ | 4.83 | 9.08 | 42.24 |
| $CH_4O$ | 2944.28 | 3928.38 | 3.17 |
| DME | 164.89 | 275.24 | 271.58 |
| $C_6H_{26}O_6$ | 0.00 | 0.00 | 1700.00 |

| Feedstocks | | | |
|---|---|---|---|
| Feedstocks | Example 1 | Example 2 | Example 3 |
| Biomass (10 wt % moisture), TPD | 438 | 445 | 464 |
| Oxygen (98 mol % pure), TPD | 162 | 164 | 170 |
| Steam, TPD | 52 | 82 | 100 |

The absorption solvent $C_{12}H_{26}O_6$ also has much higher molecular weight and boiling point than $CH_4O$ which means higher energy is required to heat, to cool and to pump the absorption solvent $C_{12}H_{26}O_6$:

| Pure Absorption Solvent Physical Properties | | | | |
|---|---|---|---|---|
| Absorption Solvent | MW | TF, °F. | TB, °F. | ΔHv, Btu/lbmol |
| $CH_4O$ | 32.04 | −143.82 | 148.46 | 15,108 |
| $C_{12}H_{26}O_6$ | 266.33 | 11.21 | 647.51 | 29,585 |

| Energy Requirement | | | |
|---|---|---|---|
| Energy Requirement | Example 1 | Example 2 | Example 3 |
| Reboiler Heat Duty, Btu/hr | $31.88 \times 10^6$ | $48.72 \times 10^6$ | $230.07 \times 10^6$ |
| To pump from 101 psig to 710 psig, hp | 157.16 | 209.57 | 855.86 |
| To cool from reboiler temp. to 14° F., Btu/hr | $20.79 \times 10^6$ | $27.74 \times 10^6$ | $212.60 \times 10^6$ |

EXAMPLE 4

Same as Example 2 except that 18.75 mol % of the cooled syngas from the autothermal reformer is passed through a water gas shift (WGS) reactor. The effluent from the WGS reactor is then combined with the remaining 81.25 mol % of the syngas in order to have a similar compressed syngas composition as in Example 2:

| Compressed Syngas Composition | | |
|---|---|---|
| Compressed Syngas Composition | Example 2 | Example 4 |
| Phase | Vapor | Vapor |
| Temp., °F. | 108.0 | 108.0 |
| Pressure, psig | 710.5 | 710.5 |
| Component Flow, lbmol/hr | | |
| $CH_4$ | 56.26 | 52.76 |
| $CO_2$ | 445.19 | 444.35 |
| $N_2$ | 9.23 | 9.24 |
| $H_2O$ | 4.79 | 4.78 |
| CO | 873.48 | 871.69 |
| $H_2$ | 930.05 | 930.94 |

Meanwhile the steam feed to the gasifier is greatly reduced:

| Steam Feed to Gasifier | | |
|---|---|---|
| Feedstocks | Example 2 | Example 4 |
| Steam, TPD | 82 | 46 |

EXAMPLE 5

Same as Example 1 except that the PSA unit for the $H_2$ recovery from the DME synthesis loop purge gas is eliminated and the whole purge gas stream is recycled to the autothermal reformer. The methane content in the purge gas is reformed to produce more $H_2$ and CO in the autothermal reformer, and less biomass, oxygen and steam are required to produce the same amount of DME product.

| Feedstocks | | |
|---|---|---|
| Feedstocks | Example 1 | Example 5 |
| Biomass (10 wt % moisture), TPD | 438 | 429 |
| Oxygen (98 mol % pure), TPD | 162 | 161 |
| Steam, TPD | 52 | 50 |

The $H_2$/CO molar ratio in the feed syngas to the DME reactor also reduces from 1.4149 to 1.0392 due to the elimination of the PSA unit for the $H_2$ recovery from the purge gas. Meanwhile the $N_2$ concentration increases from 7.70 to 19.12 mol %.

Feed Gases to DME Reactor

| Feed Gas to DME Reactor | Example 1 | Example 5 |
|---|---|---|
| Phase | Vapor | Vapor |
| Temp., °F. | 47.5 | 46.6 |
| Pressure, psig | 710.5 | 710.5 |
| Flowrate, lbmol/hr | 5302.72 | 5308.02 |
| $H_2$/CO Molar Ratio | 1.4149 | 1.0392 |
| Composition, Mol % | | |
| $CH_4$ | 13.94 | 14.00 |
| $CO_2$ | 4.87 | 4.95 |
| $N_2$ | 7.70 | 19.12 |
| $H_2O$ | 0.00 | 0.00 |
| CO | 30.40 | 30.33 |
| $H_2$ | 43.01 | 31.52 |
| $CH_4O$ | 0.06 | 0.06 |
| DME | 0.02 | 0.02 |

EXAMPLE 6

Same as Example 1 except that the pressure of the two light end columns is changed to 224.6 psig, 347.9 psig and 463.9 psig in order to increase the condenser temperature. The pressures and the resulting molar reflux ratios, temperatures and heat duties of the condensers and reboilers for these two light end columns are shown below.

LIGHT END DISTILLATION COLUMN lb1

| | | Condenser | | Reboiler | |
|---|---|---|---|---|---|
| Pressure, Bar (psig) | Molar Reflux Ratio | Temperature, °F. | Heat Duty, $10^6$ Btu/hr | Temperature, °F. | Heat Duty, $10^6$ Btu/hr |
| 8.0 (101.3) | 1.0 | −50.92 | −0.38 | 116.14 | 0.99 |
| 16.5 (224.6) | 2.0 | −18.15 | −0.65 | 175.05 | 1.55 |
| 25.0 (347.9) | 3.0 | 2.99 | −0.88 | 214.44 | 1.97 |
| 33.0 (463.9) | 4.0 | 18.13 | −1.05 | 243.40 | 2.30 |

LIGHT END DISTILLATION COLUMN lb2

| | | Condenser | | Reboiler | |
|---|---|---|---|---|---|
| Pressure, Bar (psig) | Molar Reflux Ratio | Temperature, °F. | Heat Duty, $10^6$ Btu/hr | Temperature, °F. | Heat Duty, $10^6$ Btu/hr |
| 8.0 (101.3) | 1.0 | −55.54 | −2.05 | 233.77 | 20.32 |
| 16.5 (224.6) | 2.0 | −20.46 | −3.65 | 293.31 | 28.04 |
| 25.0 (347.9) | 2.5 | 2.46 | −4.10 | 331.05 | 32.70 |
| 33.0 (463.9) | 3.0 | 19.01 | −4.43 | 357.64 | 36.31 |

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed is:

1. A process for the production of DME from carbonaceous fuel comprising the following steps:
   Simultaneously subjecting a feedstock mixture including carbonaceous fuel, steam, oxidant to a pressurized multi-stage progressively expanding fluidized bed gasifier to eliminate or reduce the formation of methane gas and tars;
   Using an oxyblown autothermal reformer to reform any residual tars and benzene-toluene-xylenes that are still present in the hot gases into additional syngas the autothermal reformer may also convert most of the methane present in the gasifier effluent stream into additional syngas;
   Recovering the heat from the reformer effluent in the syngas heat recovery boiler;
   Directing the effluent from the syngas heat recovery boiler into a water cooled heat exchanger where the bulk of the water vapor in the syngas is condensed and knocked-out;
   Compressing the cooled syngas from 130 psig to 710 psig which is the desirable pressure for the acid gas removal system;
   Directing the compressed syngas into the acid gas absorber where the acid gas content in the syngas is removed to a desirable level;
   Subjecting the treated syngas to the DME synthesis in the presence of a catalyst to obtain a reaction product gas mixture including DME, methanol, carbon dioxide, water vapor, unconverted hydrogen and carbon monoxide;
   Condensing the reaction product gas mixture to separate part of the DME product and most of the water produced;
   The balance of the DME product and most of the carbon dioxide produced is recovered by a methanol or methanol/DME absorber operating at absorber outlet temperatures ranging from −6° F. to 23° F.;
   Purifying the above two crude DME streams to obtain the fuel grade DME product.

2. The process as set forth in claim 1, wherein the pressurized multi-stage progressively expanding fluidized bed gasifier may contain a fluidizing medium that may range from sand to olivine particles.

3. The process as set forth in claim 1, wherein the oxyblown autothermal reformer may enable the maintenance of high syngas temperature, 1,436° F. to 1,562° F. for efficient heat recovery.

4. The process as set forth in claim 1, wherein the gasifier may include a plurality of stages, where the subsequent stage may have a greater cross-sectional area than the previous stage and may be in fluid communication with the previous stage.

5. The process as set forth in claim 1, wherein the pressurized gasifier may be configured such that the chemical kinetics within the reaction zone and the geometry of its multiple stages and inter-stage transitions are facilitated to reduce the formation of methane and tars.

6. The process as set forth in claim 1, wherein the steam and oxidant flow rates to the gasifier are adjusted to maintain the gasifier operating temperature, meanwhile desirable hydrogen to carbon monoxide molar ratio for the DME synthesis is also obtained.

7. The process as set forth in claim 6, wherein a water gas shift reactor may be added after the autothermal reformer to shift part of the syngas produced in order to reduce the flowrate of steam fed to the gasifier.

8. The process as set forth in claim 1, wherein a physical solvent $C_{12}H_{26}O_6$ is used in the absorber to remove acid gases from the make-up syngas the rich solvent exiting the acid gas absorber can be flash regenerated and then pumped back to the absorber for reuse.

9. The process as set forth in claim 1, wherein a fluid pluralized bed reactor is used for the DME synthesis the reactor, the feed gases are introduced in controlled quantities at several sections along the reactor vertical wall in order to bring the reactor somewhat closer to an isothermal mode.

10. The process as set forth in claim 1, wherein about 75% of the hydrogen content in the purge stream from the DME synthesis loop may be recovered via a PSA unit the recovered hydrogen is then combined with the fresh make-up syngas.

11. The process as set forth in claim 1, wherein the vent from the PSA unit may be fed to the autothermal reformer, thus the methane content in the vent stream is reformed to produce additional hydrogen and carbon monoxide, meanwhile, the hydrogen and carbon monoxide in the vent stream are conserved.

12. The process as set forth in claim 1, wherein the PSA unit for the hydrogen recovery from the DME synthesis loop purge gas may be eliminated and the whole purge gas stream may be recycled to the autothermal reformer to reform the methane content and conserve the hydrogen and carbon monoxide content in the purge gas stream.

13. The process as set forth in claim 1, wherein it is advantageous to use the methanol/DME mixture which contains about 1.25 wt % of DME instead of pure methanol as the scrubbing solvent in terms of saving both refrigerating and heating energy.

* * * * *